(12) United States Patent
Lange (10) Patent No.: US 6,786,907 B2
(45) Date of Patent: Sep. 7, 2004

(54) INSTRUMENTATION FOR STABILIZING CERTAIN VERTEBRAE OF THE SPINE

(75) Inventor: Robert Lange, Paris (FR)

(73) Assignee: Co-Ligne AG, Zürich (CH)

(*) Notice: Subject to any disclaimer, the term of this patent is extended or adjusted under 35 U.S.C. 154(b) by 0 days.

(21) Appl. No.: 10/127,677

(22) Filed: Apr. 23, 2002

(65) Prior Publication Data

US 2002/0169450 A1 Nov. 14, 2002

(30) Foreign Application Priority Data

Apr. 24, 2001 (EP) .............................. 01810401

(51) Int. Cl.$^7$ ......................... A61B 17/56; A61B 17/58; A61F 2/30
(52) U.S. Cl. ........................................ 606/61; 606/72
(58) Field of Search ............................. 606/60, 61, 72, 606/73

(56) References Cited

U.S. PATENT DOCUMENTS

| | | | |
|---|---|---|---|
| 5,108,399 A | | 4/1992 | Eitenmuller et al. |
| 5,486,174 A | * | 1/1996 | Fournet-Fayard et al. ..... 606/61 |
| 5,498,263 A | * | 3/1996 | DiNello et al. ............... 606/61 |
| 5,601,554 A | * | 2/1997 | Howland et al. ............. 606/61 |
| 6,004,349 A | * | 12/1999 | Jackson ........................ 623/17 |
| 6,086,588 A | * | 7/2000 | Ameil et al. ................. 606/61 |
| 6,234,705 B1 | * | 5/2001 | Troxell ........................ 403/237 |
| 6,283,967 B1 | * | 9/2001 | Troxell ........................ 606/61 |
| 6,368,320 B1 | * | 4/2002 | Le Couedic et al. ......... 606/61 |

FOREIGN PATENT DOCUMENTS

| | | |
|---|---|---|
| EP | 0 384 001 A1 | 8/1990 |
| EP | 0 590 745 A2 | 4/1994 |
| EP | 0 923 908 A1 | 6/1999 |
| FR | 2 615 095 A1 | 11/1988 |
| FR | 2 702 361 A1 | 9/1994 |
| FR | 2 765 093 A1 | 12/1998 |
| WO | WO 94/28831 A1 | 12/1994 |
| WO | WO 98/43551 A1 | 10/1998 |

* cited by examiner

Primary Examiner—Kevin Shaver
Assistant Examiner—Anuradha Ramana
(74) Attorney, Agent, or Firm—Browdy and Neimark, P.L.L.C.

(57) ABSTRACT

The instrumentation includes a spinal stabilizing longitudinal element (1) that is adapted to be placed in a generally parallel relationship with the portion of the spine (A) to be treated, a connector (6) having an opening (7) therethrough, a mechanism (10) is adapted to affix said bone-anchoring element (2) in the opening (7); the connector (6) has a hook portion (11) adapted to cooperate with a support (32) of the bone-anchoring element (2) for clamping the longitudinal element (1); the hook portion (11) has at its bottom side a recess (12) for receiving the longitudinal element (1); the longitudinal element (1) is clamped against said support (32), so that the force of the support (32) on the longitudinal element (1) is approximately parallel to the axis (D) of the bone-anchoring element (2).

8 Claims, 11 Drawing Sheets

INSTRUMENTATION FOR STABILIZING CERTAIN VERTEBRAE OF THE SPINE

BACKGROUND OF THE INVENTION

1. Technical Field of the Invention

The invention relates to an instrumentation for stabilizing certain vertebrae of the spine.

2. Prior Art

Instrumentations are known whose aim is to stabilize the spine after surgical treatment of spinal problems. Many of these instrumentations include rods positioned parallel to the spine that carry pedicle screws via a connector. For instance, the EP-A-0 923 908 (Lange) is directed to an instrumentation having a C-clamp that has a jaw at one end thereof which can be quickly and efficiently tightened about a smooth rod. The C-clamp carries a pedicle screw along the rod for coarse positioning and having a means to permit a pivoting movement between the pedicle screw and a connector for fine adjustment while maintaining a fixed reference distance between the rod and the pedicle screw pivot point at all times.

WO98/43551 (Chopin et al) discloses an instrumentation comprising a connector for fastening a rod to a bone-anchoring element. The bone-anchoring element has a anchoring support for the rod, inclined with respect to the longitudinal axis of the bone-anchoring element. The connector has a recess which provides at least one support point for the rod.

In all spinal operations the skill of the surgeon is constantly challenged. The repair and reconstruction work that must be done is located next to vital nerve structures and each patient's spine is different in some respect. In order to treat certain spine pathologies, it is oftentimes required to fix one vertebrae with respect to an adjacent or remote vertebrae in a procedure called the spinal fusion or arthrodieses.

OBJECT AND SUMMARY OF THE INVENTION

The instrumentation according to the above noted state of the art fixedly secures the vertebrae together that are on either side of the injured portion of the spine. The instrumentation should restrain the vertebrae from rotation or left to right, back to front, or up and down motions with respect to one another. The vertebrae are fixed in space with respect to one another until fusion occurs, that is the two fixed vertebrae grow together to form one continues form.

A principle objective of the present invention is to provide an instrumentation which further facilitates the use of the instrumentation for surgeons and which nevertheless has few parts. The instrumentation is provided with a connector that has a hook portion adapted to cooperate with a support of the bone-anchoring element for clamping the longitudinal element, said hook portion having at its bottom side a recess for receiving the longitudinal element, said longitudinal element is clamped against said support, whereas the force of the support on the longitudinal element is approximately parallel to the axis of the bone-anchoring element. The instrumentation of the present invention has the advantage, that more force can be applied to the longitudinal element and that it can be manufactured with a lower profile. Furthermore, the instrumentation of the present invention gives the surgeon the option to use composite materials for the longitudinal element which is radiolucent and can be configured to have mechanical properties closer to bone than traditional materials such as titanium or steel. Furthermore, the instrumentation gives the surgeon the option of a lower profile and polyaxiality of the anchoring mechanism in relationship to the longitudinal element.

BRIEF DESCRIPTION OF THE DRAWINGS

Further features of the present invention will become apparent to those skilled in the art to which the present invention relates from reading the following specification with reference to the accompanying drawings, in which:

FIGS. 14a to 18a and 14b to 18b illustrate different stages of the cross connector according to FIGS. 12 and 13, during its assembly in situ, that is during the surgery, and FIGS. 19a and 19b overall views showing the relationship of the instrumentation with respect to the spine cord.

DETAILED DESCRIPTION OF THE PREFERRED EMBODIMENT(S) OF THE INVENTION

Figure 16A:
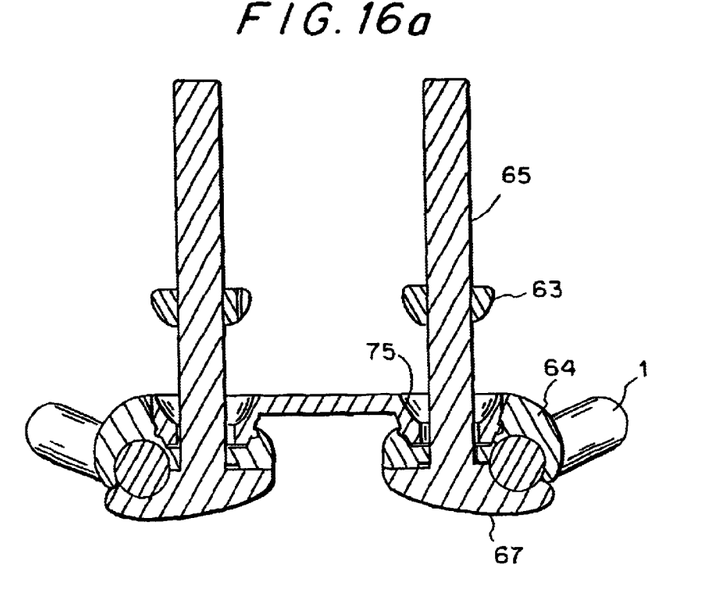
Figure 16B:
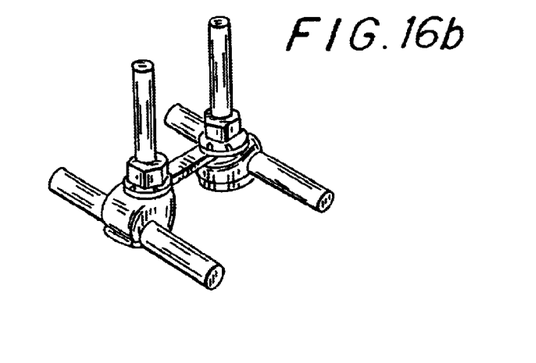
Figure 17A:
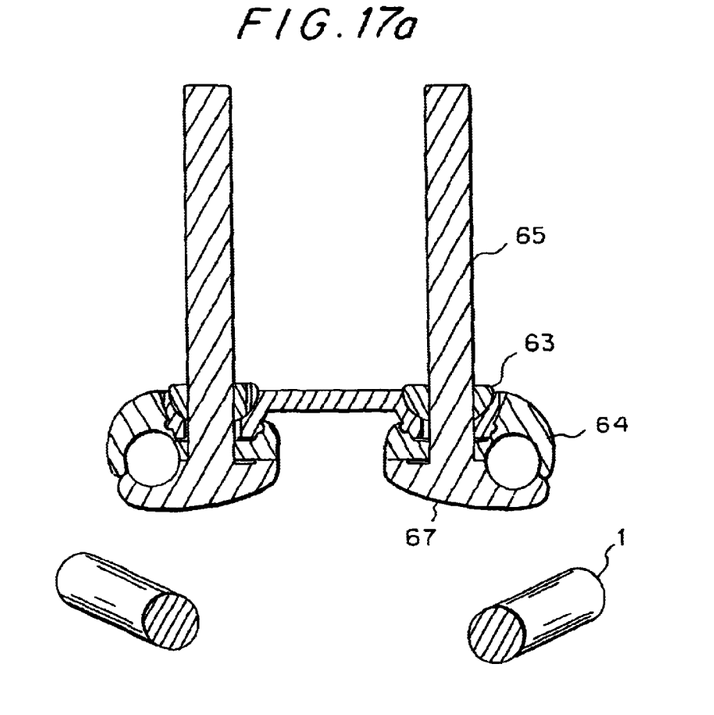
Figure 17B:
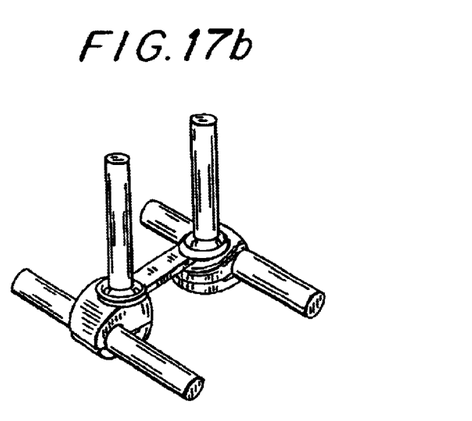
Figure 18A:
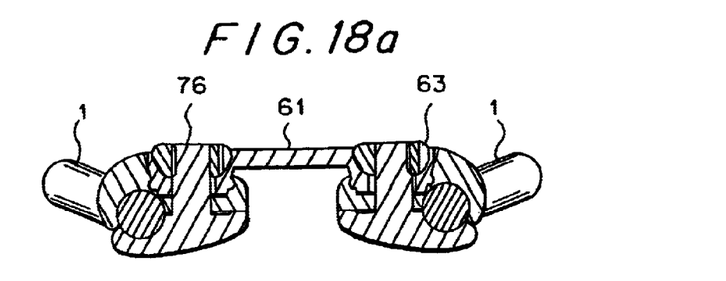
Figure 18B:
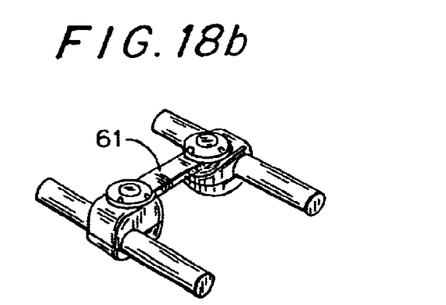
Figure 19A:
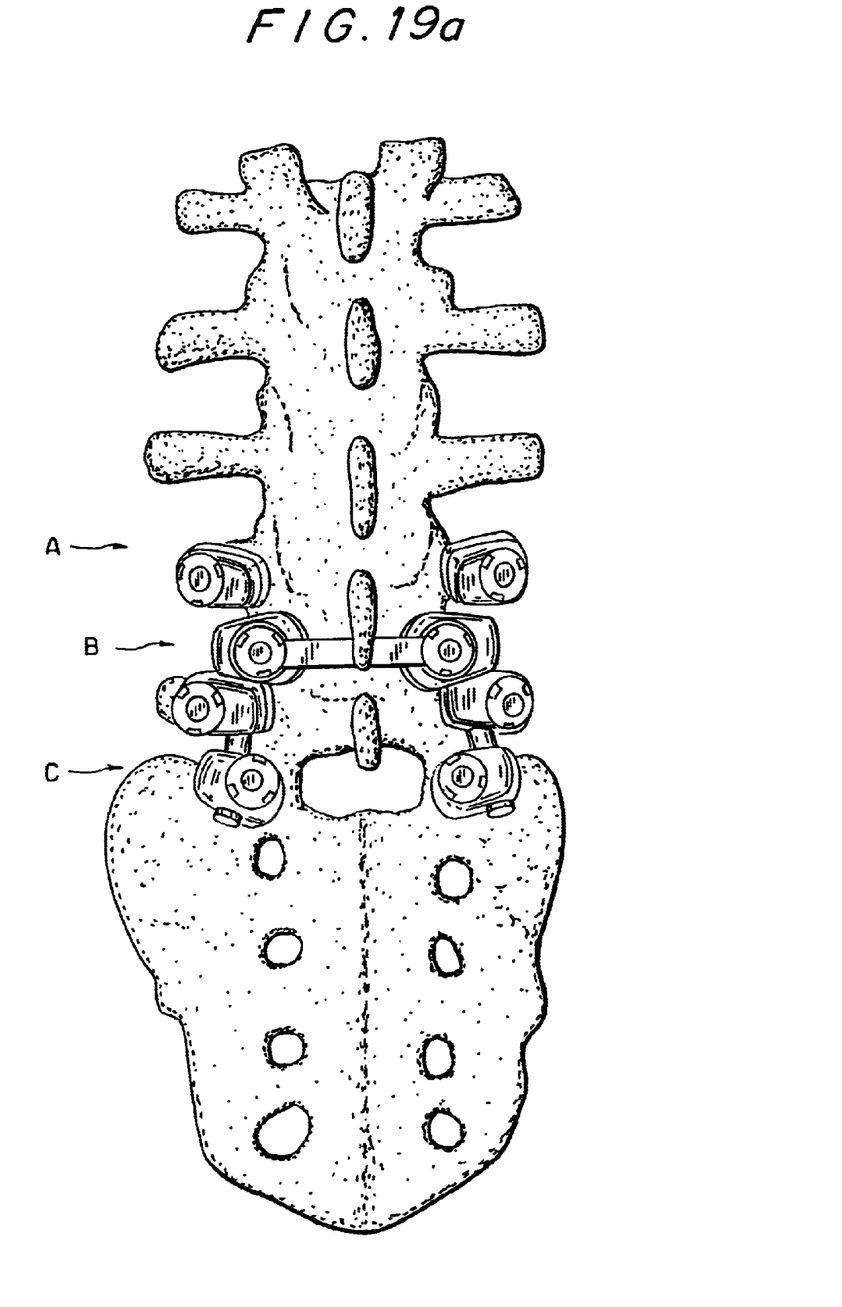
Figure 19B:
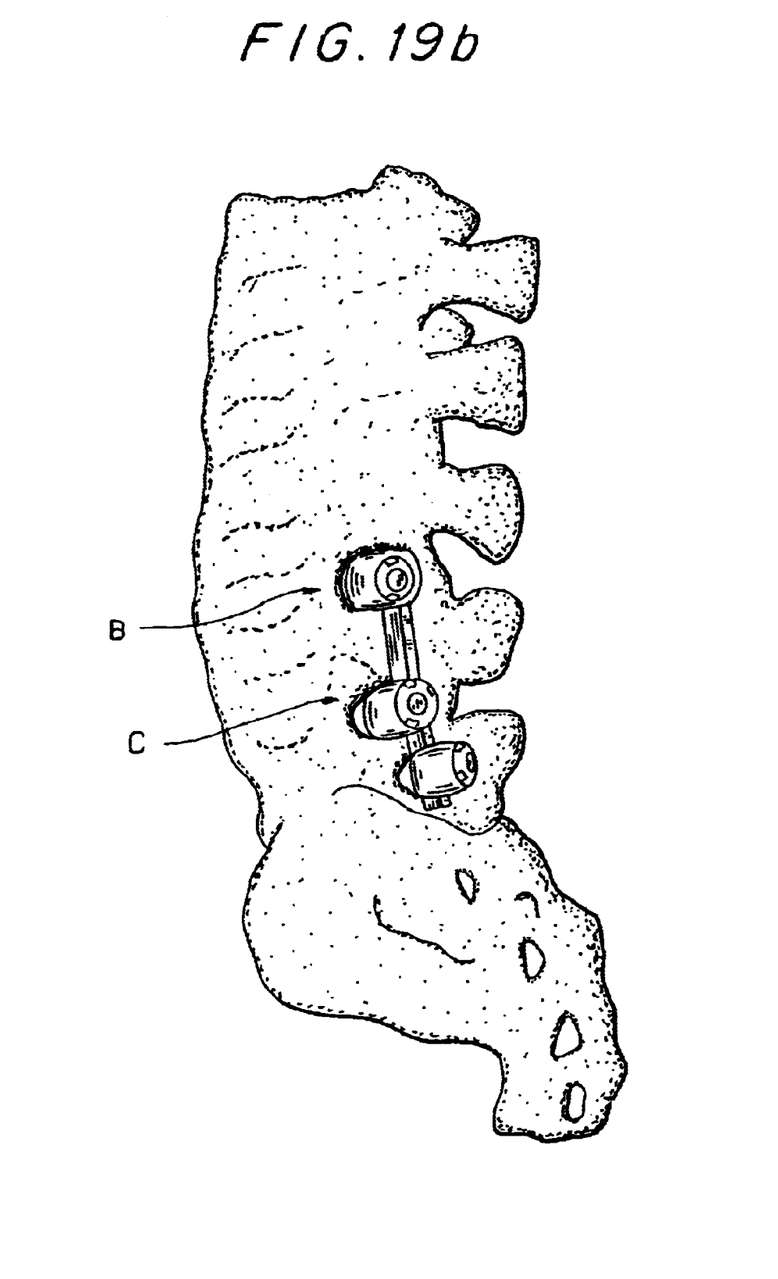

The instrumentation illustrated in FIGS. 1 to 5 comprises a pedicle screw 2, a nut 10, a connector 6, a upper slip washer 14 and a lower slip washer 13. The pedicle screw 2, from top to bottom (as viewed in FIGS. 1 and 2), consists of a threaded section 4, a curvilinear shoulder 38, a hexagonal nut 5 and a cancellous type thread section 3. The pedicle screw 2 is received by an opening 7 formed in the connector 6. The nut can be a break-away nut 63' as seen in FIGS. 14b to 18b. This nut 63' has a upper part 63'a (FIG. 15b) that is broken off after the nut 63' has been clamped as seen in FIG. 16b.

The connector 6 is comprised of a hook portion 11 having a recess to grasp a smooth round spinal stabilizing rod 1. The hook portion two opposing ridges 8 and 9, which have a distance to each other, which is shorter than the diameter of the rod 1. The two ridges 8 and 9 provide snap-on means when the rod 1 is moved into the recess.

Figures 4, 5:
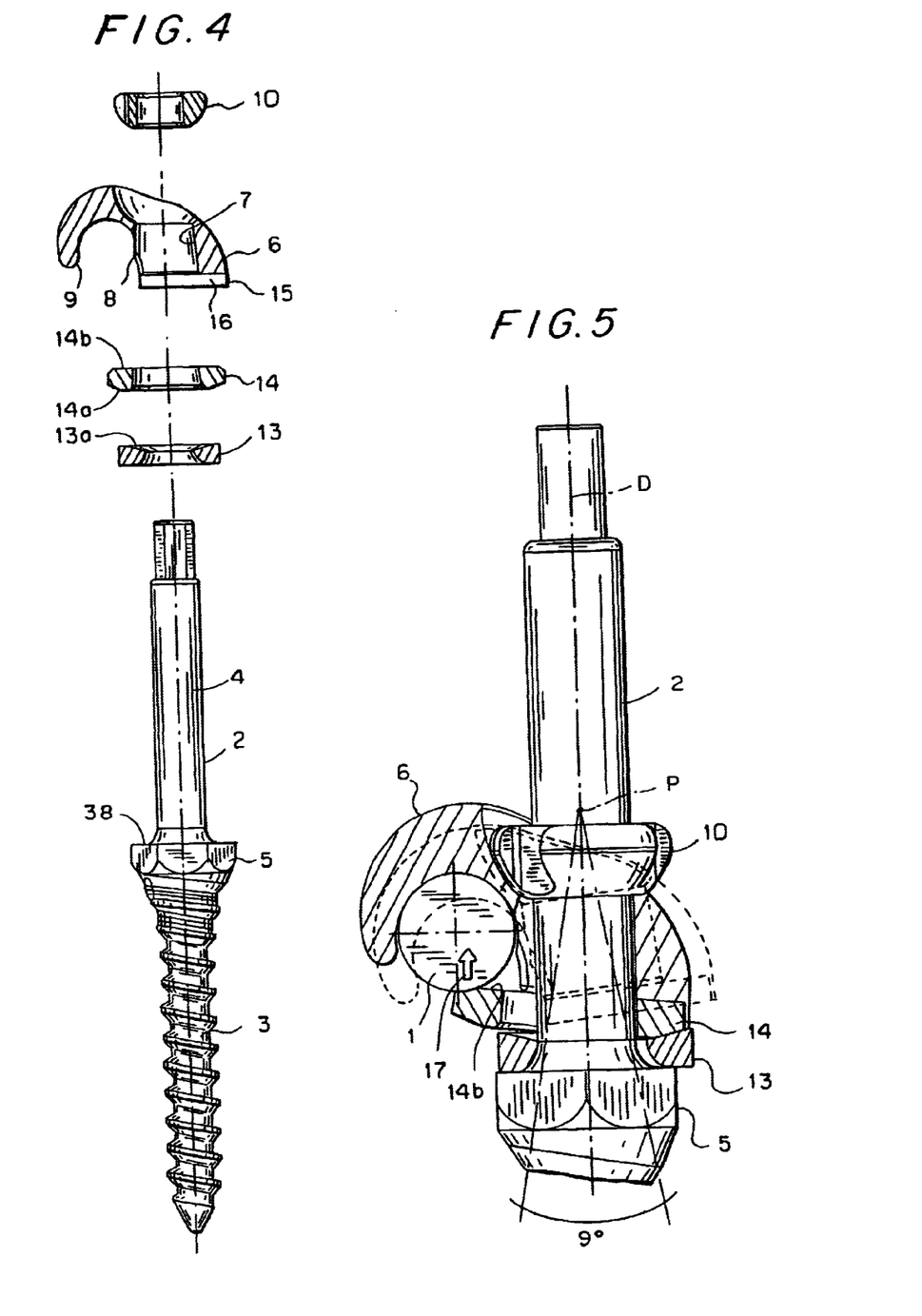
FIG. 4 is an exploded side elevation of several components of the instrumentation according to the present invention.
FIG. 5 is a side view partly in section of the components shown in FIG. 4 in there assembled relationship.

The lower washer 13 is slipped over the thread section 4 and rests against an upper surface 38 adjacent to a hexagonal nut 5. The lower washer 13 has a peripheral upper concave surface 13a and remains longitudinally stationary with respect to the pedicle screw 2. The slip upper washer 14 is also slipped over the thread 4. Washer 14 engages lower slip washer 13 and has a bottom convex surface 14a for engagement with the concave surface 13a. As FIG. 5 shows, the surfaces 13a and 14a can slide with respect to one another about a center point P. An upper surface 14b rests against a horseshoe shape surface 16 of the connector 6. A flange 15 at the periphery of the surface 16 supports the slip washer 14.

Figure 1:
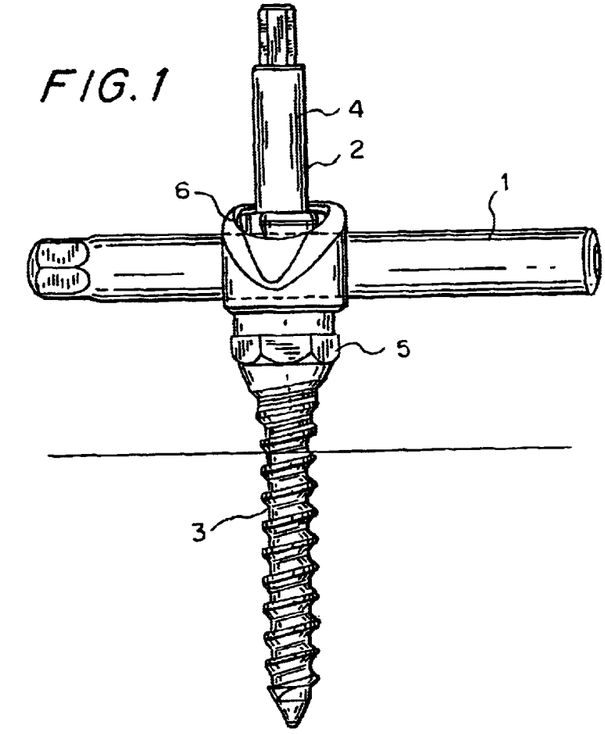
FIG. 1 is a side view of the instrumentation according to the present invention.
Figure 2:
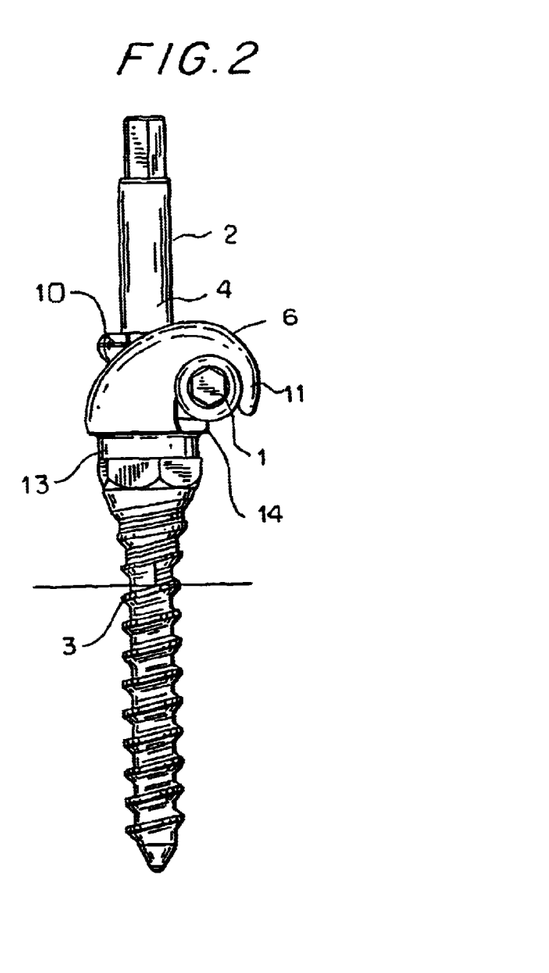
FIG. 2 is another side view of the instrumentation shown in FIG. 1.
Figure 3:
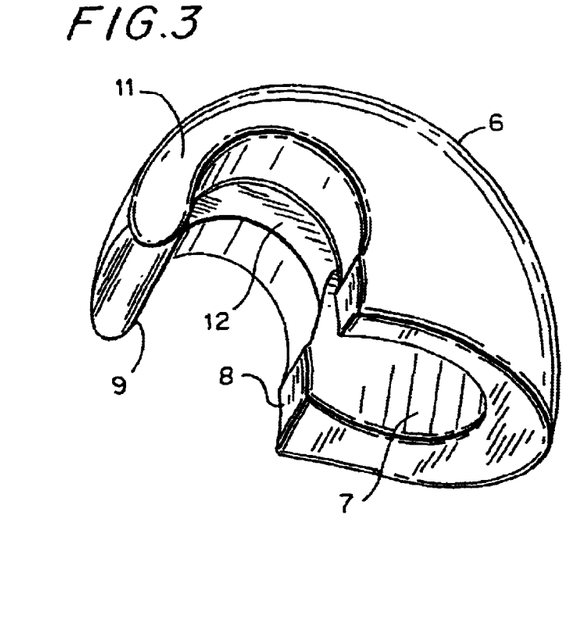
FIG. 3 is an enlarged perspective view of a portion the instrumentation illustrated in FIGS. 1 and 2.

The rod 1 is permitted to slide longitudinally with respect to the pedicle screw 2 prior to tightening. After the rod 1 is located, the nut 10 is tightened and the rod 1 is clamped and secured between the slip washer 14 and the connector. As seen in FIGS. 2 and 5, the rod 1 rests on the surface 14b of the slip washer 14. The force of the slip washer 14 on the rod 1 is approximately parallel to the axis D as indicated in FIG. 5 with the arrow 17. As the force is approximately parallel to the axis D, more force can be exerted on the rod 1 compared with an another direction of a force exerted on the rod 1. This enables to apply more clamping force to the rod 1 and to manufacture the connector small and with a very low profile. Furthermore a polyaxial configuration is possible, which enables to pivot the connector 6 about point P in all directions as seen in FIG. 5.

Figures 6, 7:
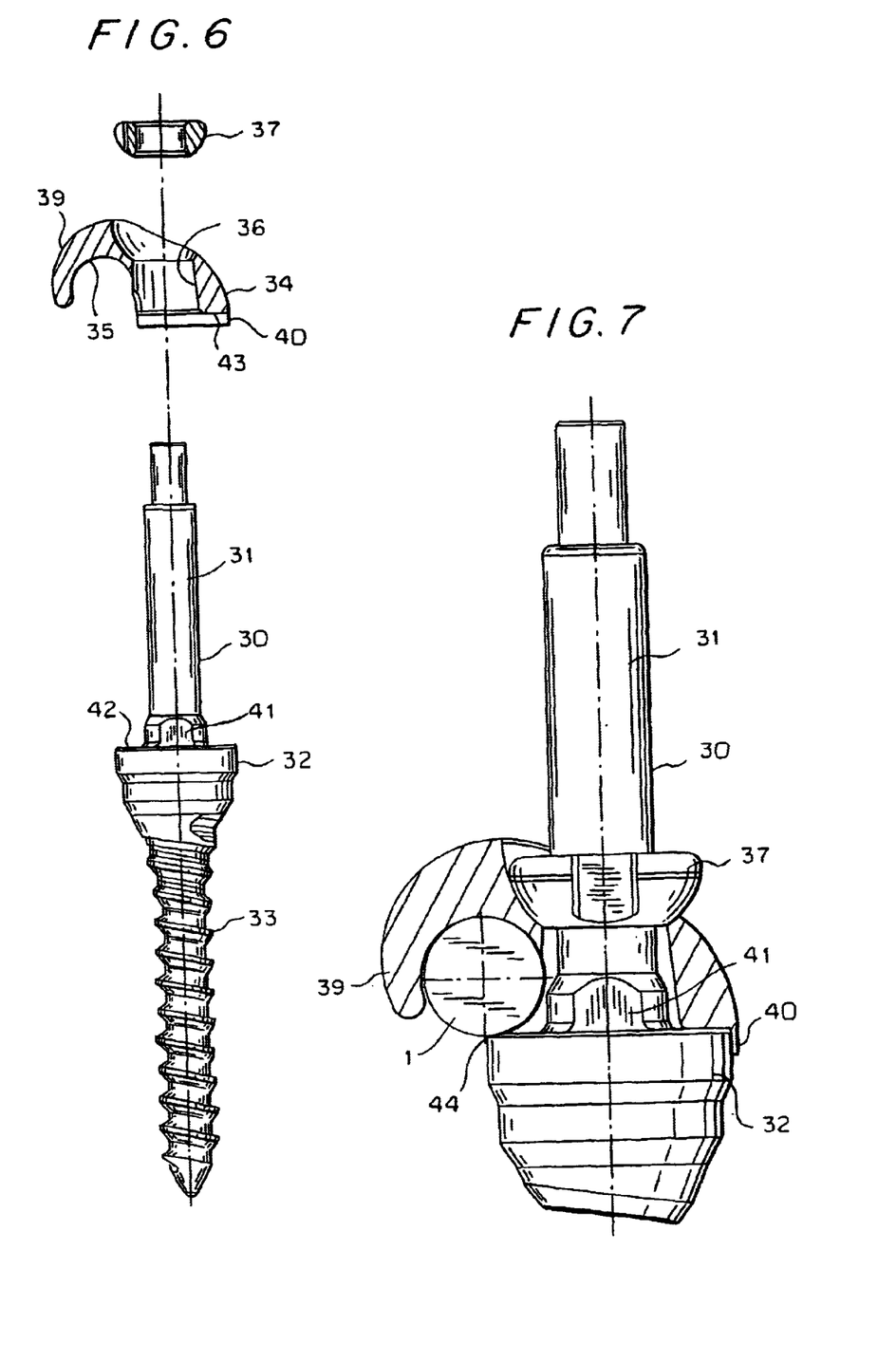
FIG. 6 is an exploded side elevation of several components of the instrumentation according to another embodiment of the present invention.
FIG. 7 is a side view partly in section of the components shown in FIG. 6 in there assembled relationship.

The embodiment according to FIGS. 6 and 7 comprises a pedicle screw 30 having thread sections 31 and 33 and there between a widening or support 32. The support 32 has an upper surface, which is perpendicular to the axis of the pedicle screw 30 and which rests against a surface 43 at the bottom of a connector 34. Two opposing flats 41 for engagement with a not shown tool are formed near the surface 42. The connector 34 has an opening 36 for receiving the thread section 31, a hook portion 39 and a supporting flange 40. The hook part 39 is provided with a recess 35 that receives the rod 1 as seen in FIG. 7. The rod 1 is clamped between the support 32 and the connector 34 wherein the force of the support on the rod 1 is parallel to the axis D. The support 32 engages the rod 1 at a point 44 at the lower side of the rod 1. This embodiment does not enable a pivoting movement of the pedicle screw 30, but as no washers are needed, it has fewer parts and is strong and compact.

Figure 8:
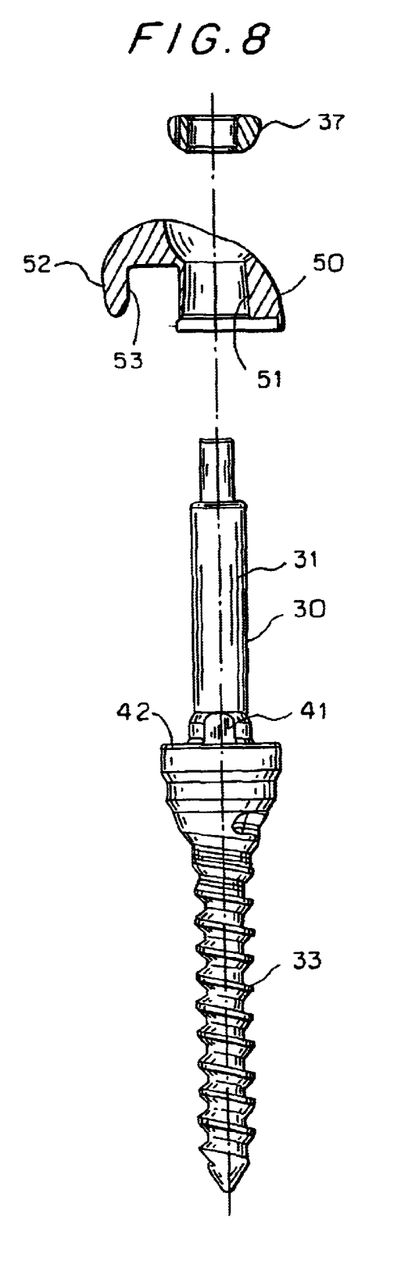
FIG. 8 is an exploded side elevation of several components of the instrumentation according to another embodiment of the present invention.
Figure 9:
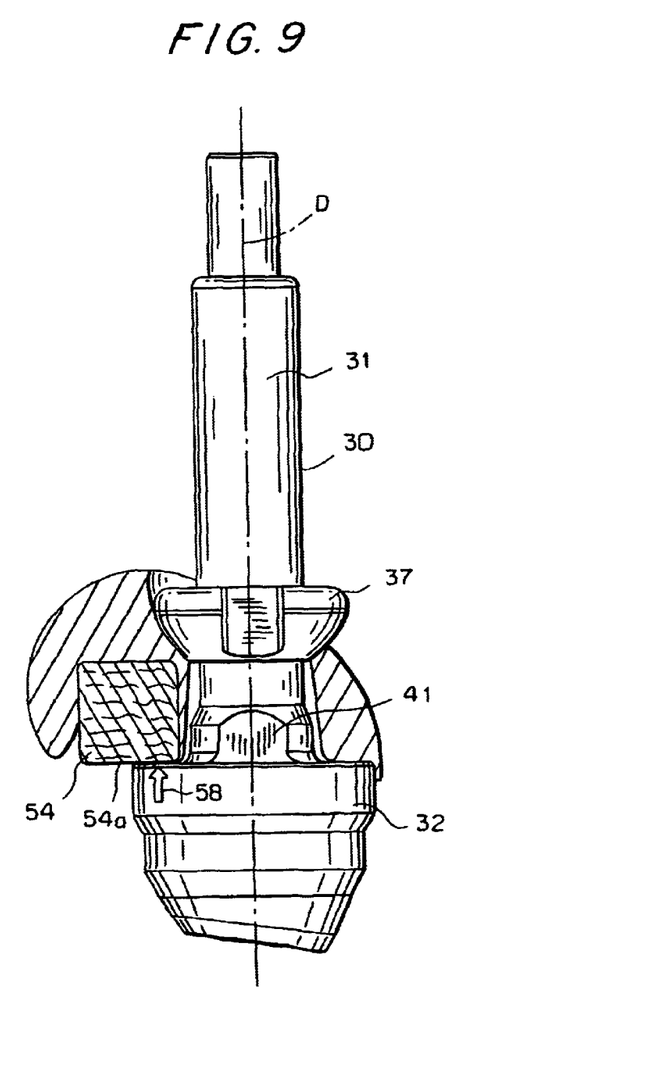
FIG. 9 is a side view partly in section of the components shown in FIG. 8 in there assembled relationship.

FIGS. 8 and 9 disclose an embodiment that comprises a pedicle screw 30 as described above, a nut 37 and a connector 50. The connector 50 has an opening 51, a hook part 52 and a recess 53 for receiving a rail 54 that has a rectangular cross section as seen in FIG. 9. The surface 42 engages the rail 54 at a lower side 54a and the force applied on the rail 54 has a direction that is parallel to the axis D of the pedicle screw 30, as indicated in FIG. 9 with arrow 58. The rail is made of stainless steel, titanium or plastic and preferably a composite material containing long carbon fibers.

Figure 10:
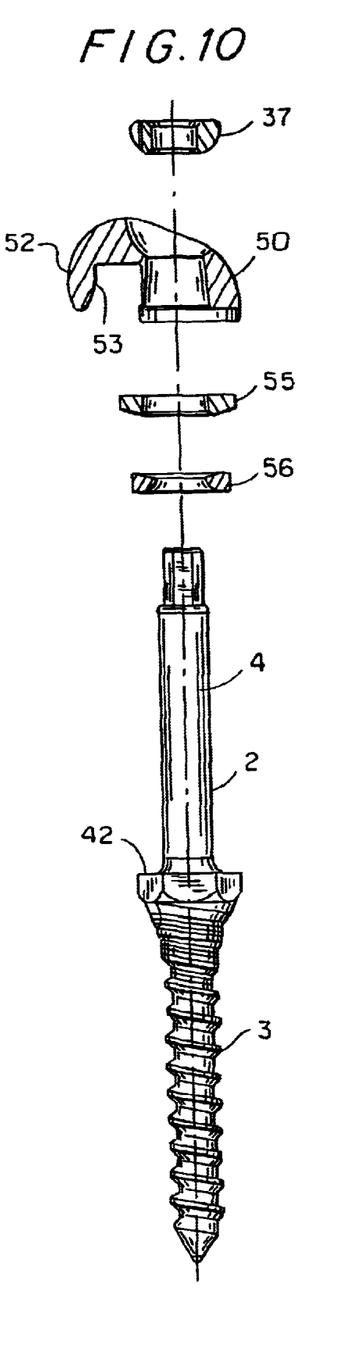
FIG. 10 is an exploded side elevation of several components of the instrumentation according to another embodiment of the present invention.
Figure 11:
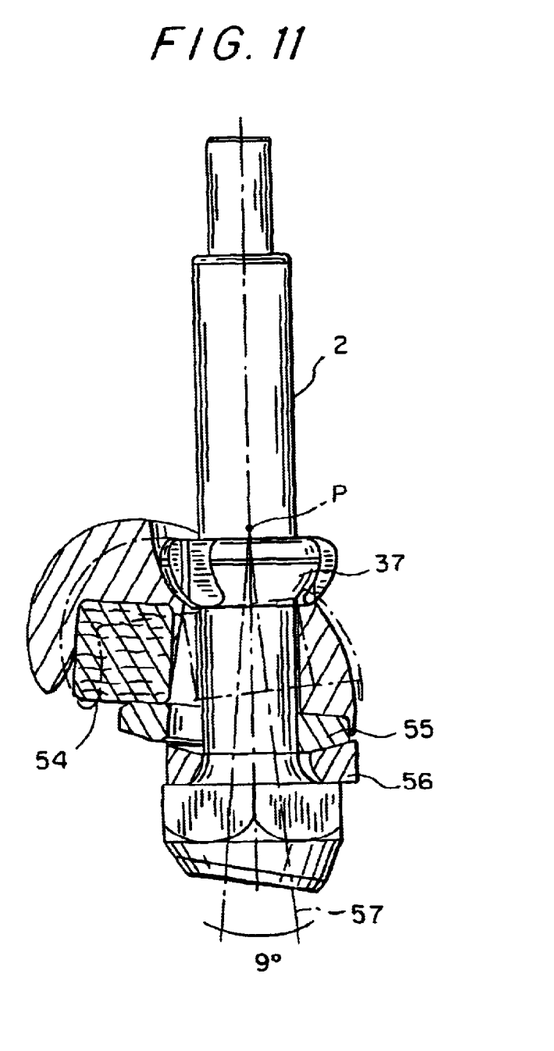
FIG. 11 is a side view partly in section of the components shown in FIG. 10 in there assembled relationship.

The embodiment according to FIGS. 10 and 11 is similar to that disclosed in FIGS. 8 and 9 but is provided with a lower washer 56 and a slip washer 55 and does enable a pivoting movement of the pedicle screw 2.

FIGS. 12 to 19 disclose a transverse connector 60 for connecting two rods 1. The connector 60 includes a pair of fixing means 62 and a transverse element 61 connecting the fixing means 62. The transverse element 61 has in a distance to each other two recesses 75 each receiving a nut 63 and a pair of openings 77 each receiving a foot element 65. Each fixing means 62 comprises an upper clamping element 64 that has at its upper side a tapered recess receiving a corresponding connecting part 79 formed at the transverse element 61. At the tapered outer surface of the connecting part 79 a circumferential rip 72 is formed, that engages a corresponding groove 80 of the clamping element 64. Each clamping element 64 is rotatably fixed at the transverse element 61.

Figure 12:
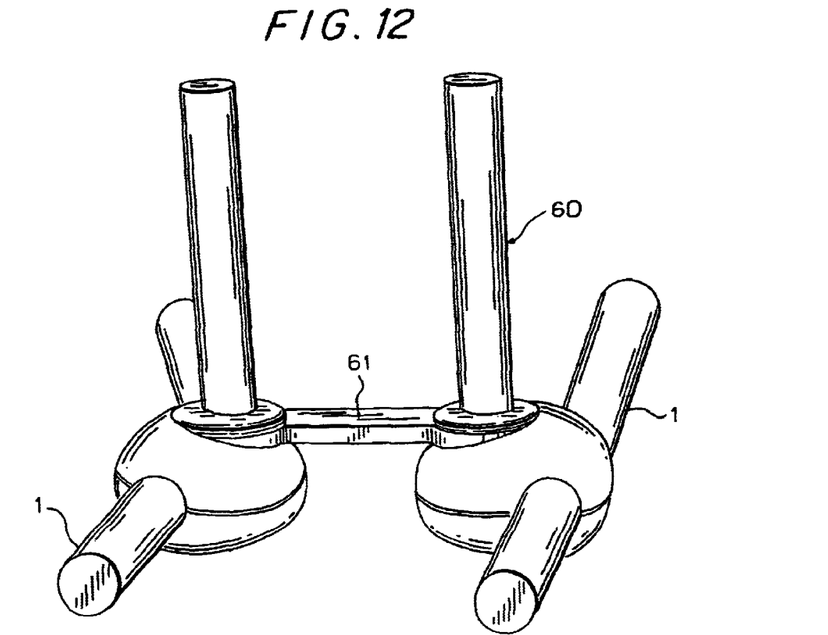
FIG. 12 is a perspective view of a cross connector.
Figure 13:
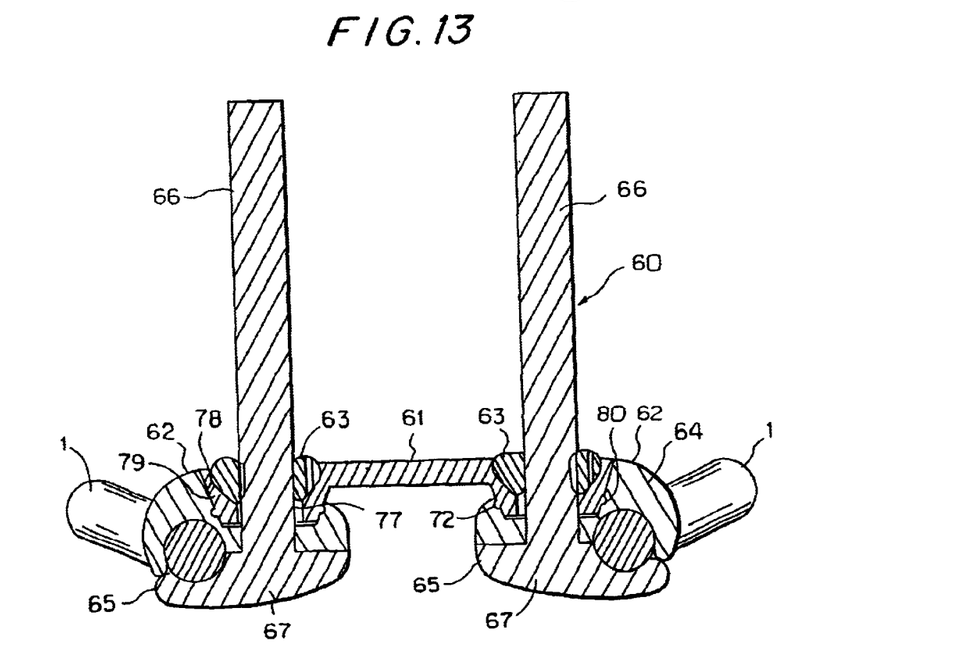
FIG. 13 is a vertical cross section of the cross connector according to FIG. 12.

Each of the foot elements 65 comprises a clamping part 67 having a recess 68 for receiving a rod 1, a rod like grip 66 and an elevated surface 70 engaging a surface 71 at the lower side of a clamping element 64.

Figure 14A:
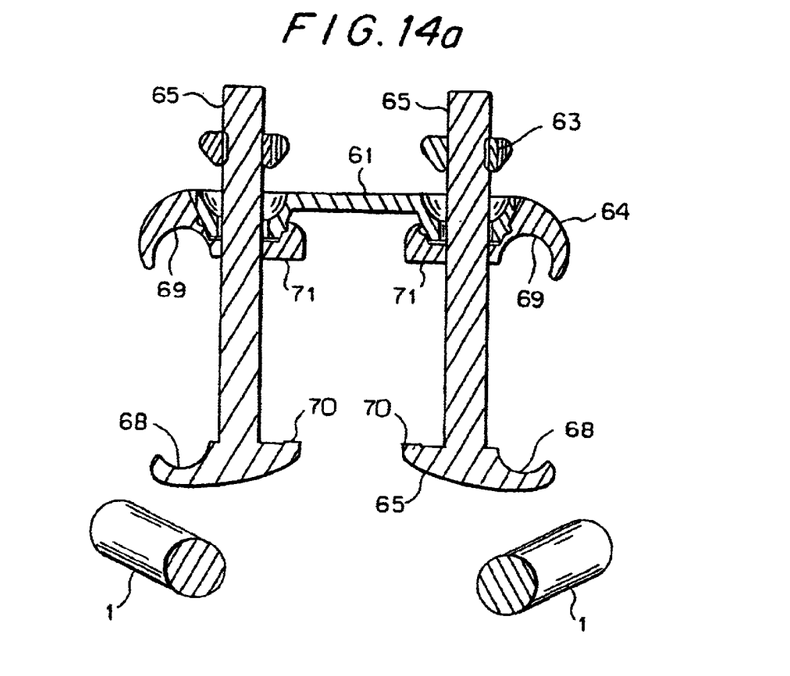
Figure 14B:
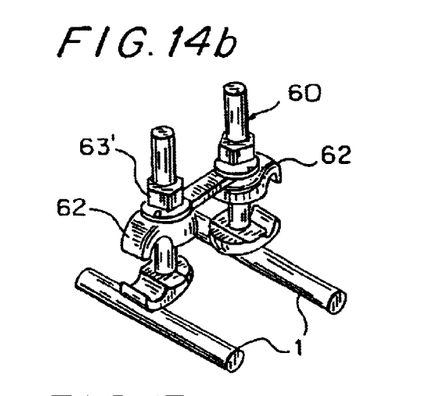
Figure 15A:
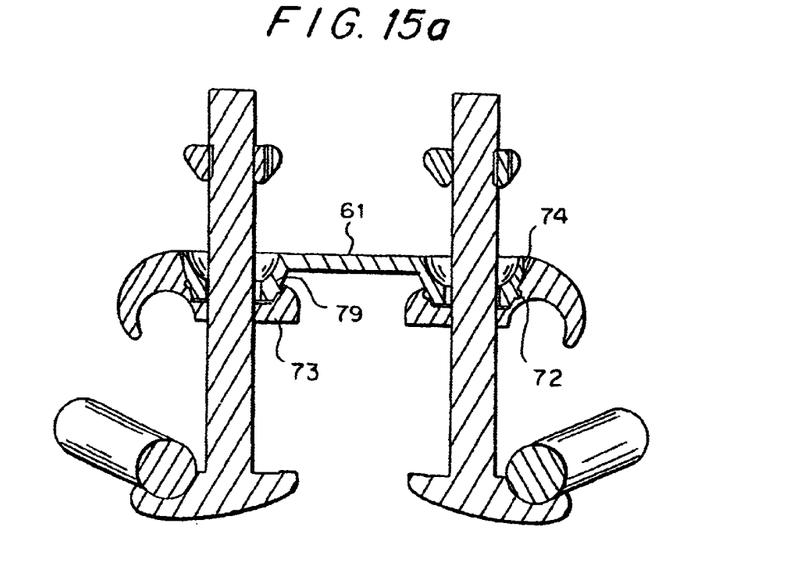
Figure 15B:
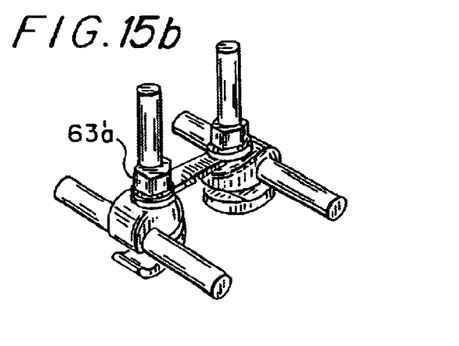

The transverse connector 60 is attached to the rods as illustrated in FIGS. 14 to 19. In FIG. 14, the two rods 1 are fixed to the spine with pedicle screws or any other bone-anchoring element and connectors as disclosed above. At least one rod 1 can also be a rail 54 or any other longitudinal element suitable to connect two vertebrae. The nuts 63 and the transverse element 61 are positioned as seen in FIG. 14. The recesses 68 and 69 are spaced apart and the foot elements 65 are pivotable at a point located above the transverse element 61.

What is claimed is:

1. An instrumentation for stabilizing certain vertebrae of the spine with respect to one another in a portion of the spine to be treated, the instrumentation comprising:

a spinal stabilizing longitudinal element that is adapted to be placed in a generally parallel relationship with the portion of the spine to be treated;

a bone-anchoring element;

a connector having an opening therethrough, said opening having dimensions greater than a cross-section dimension of a machine thread section of said bone-anchoring element;

a mechanism adapted to affix said bone-anchoring element in said opening;

said mechanism comprising a pressure element received by said bone-anchoring element;

wherein said connector has a hook portion adapted to cooperate with a support of the bone-anchoring element for clamping the longitudinal element;

said hook portion having at a bottom side thereof a recess for receiving the longitudinal element;

wherein said hook portion is provided with snap-on means when the longitudinal element is moved into the recess;

wherein when said longitudinal element is clamped against an upper surface of said support said upper surface is perpendicular to an axis of the bone-anchoring element and a force of the support and the connector on the longitudinal element is approximately parallel to the axis of the bone-anchoring element.

2. An instrumentation according to claim 1, wherein the longitudinal element engages a washer received by said bone-anchoring element and arranged between said connector and said support.

3. An instrumentation according to claim 2, wherein the washer has an opening therethrough, said opening having dimensions greater than a cross-section dimension of said bone-anchoring element.

4. An instrumentation according to claim 2, wherein said connector has on a bottom side thereof a recess adapted to receive a section of the washer.

5. An instrumentation according to claim 2, wherein the washer is a slip washer.

6. An instrumentation according to claim 1, comprising a transverse connector located between a first and a second longitudinal element;

said transverse connector comprising a transverse element and a first and a second fixation means for connecting the transverse element to said first and second longitudinal element:

said first and second fixation means comprising an first and upper clamping part and a second part;

said second part having a foot part clamped against a bottom side of the longitudinal element.

7. An instrumentation according to claim 6, wherein the foot part has a grip received in a opening of said first and upper clamping part.

8. An instrumentation according to claim 7, wherein said grip has a recess adapted to break at a predetermined force.

* * * * *